United States Patent [19]

Tittmann et al.

[11] 4,372,163
[45] Feb. 8, 1983

[54] ACOUSTIC MEASUREMENT OF NEAR SURFACE PROPERTY GRADIENTS

[75] Inventors: Bernhard R. Tittmann; Lloyd A. Ahlberg; Richard K. Elsley, all of Thousand Oaks, Calif.

[73] Assignee: Rockwell International Corporation, El Segundo, Calif.

[21] Appl. No.: 231,061

[22] Filed: Feb. 3, 1981

[51] Int. Cl.³ ............................................. G01N 29/00
[52] U.S. Cl. ........................................ 73/602; 73/597; 73/599
[58] Field of Search ....................... 367/25, 32, 75, 48, 367/49; 181/102; 73/597, 599, 602

[56] References Cited

U.S. PATENT DOCUMENTS

| | | |
|---|---|---|
| 2,439,130 | 4/1948 | Firestone . |
| 3,309,914 | 3/1967 | Weighart . |
| 3,504,532 | 4/1970 | Muenow et al. . |
| 3,512,400 | 5/1970 | Lynnworth . |
| 3,588,800 | 6/1971 | Moore .................................. 367/86 |
| 3,720,098 | 3/1973 | Dixon . |
| 3,847,016 | 11/1974 | Ziedonis . |
| 3,924,454 | 12/1975 | McElroy et al. . |
| 3,958,450 | 5/1976 | Kleesattel . |
| 4,137,779 | 2/1979 | Wustenberg et al. . |
| 4,313,070 | 1/1982 | Fisher .................................. 73/644 |

OTHER PUBLICATIONS

Bucaro, et al., Rayleigh Wave Dispersion on Surface--Treated Glass, 43 J. Appl. Phys. 2151 (1972).
Richardson, et al., Deducing Subsurface Property Gradients from Surface Wave Dispersion Data, 1975 IEEE Ultrasonics Symposium Proceedings 488.
Richardson, et al., Estimation of Surface Layer Structure from Rayleigh Wave Dispersion, 48 J. Appl. Phys. 498 (1977).
Richardson, et al., Estimation of Surface Layer Structure from Rayleigh Wave Dispersin, 48 J. Appl. Phys. 5111 (1977).
Richardson, et al., Estimation of Surface Layer Structure from Rayleigh Wave Dispersion, 49 J. Appl. Phys. 5242 (1978).
Szabo, Obtaining Subsurface Profiles from Surface-Acoustic-Wave Velocity Dispersion, 46 J. Appl. Phys. 1448 (1975).
Tittmann, A Technique for Precision Measurements of Elastic Surface Wave Properties on Abritrary Materials, 42 Rev. Sci. Inst. 1136 (1971).
Tittmann, et al., Use of the Impulse Technique for Rapid Texture Evaluation in Commercial Tube and Plate Materials, 74 Met. Trans. 229 (1976).
Tittmann, et al., Characterization of Subsurface Anomalies by Elastic Surface Wave Dispersion, 1974 IEEE Ultrasonics Symposium Proceedings 561.

*Primary Examiner*—Howard A. Birmiel
*Attorney, Agent, or Firm*—H. Fredrick Hamann; Craig O. Malin; John J. Deinken

[57] ABSTRACT

Disclosed is a method for determining the dispersion of a surface acoustic wave in an object, including the steps of generating a broadband acoustic wave in a surface of the object, detecting the wave at first location on the surface, and detecting the wave at a second location on the surface. Fourier transforms of the first and second detected waves are calculated, then the change in phase $\Delta\phi(f)$ of the frequency component f of the detected wave, between the first and second locations, is computed from the phase components of the quotient of the two transforms. The dispersion of the wave in the surface is given by the formula $$v(f) = (2\pi f \, \Delta l / \Delta \phi(f))$$

In a pulse-echo version of the method, the wave is generated and detected at the first location, and generated and detected at the second location, the dispersion then being according to the formula $$v(f) = 4\pi f \, \Delta l / \Delta \phi(f)).$$

9 Claims, 11 Drawing Figures

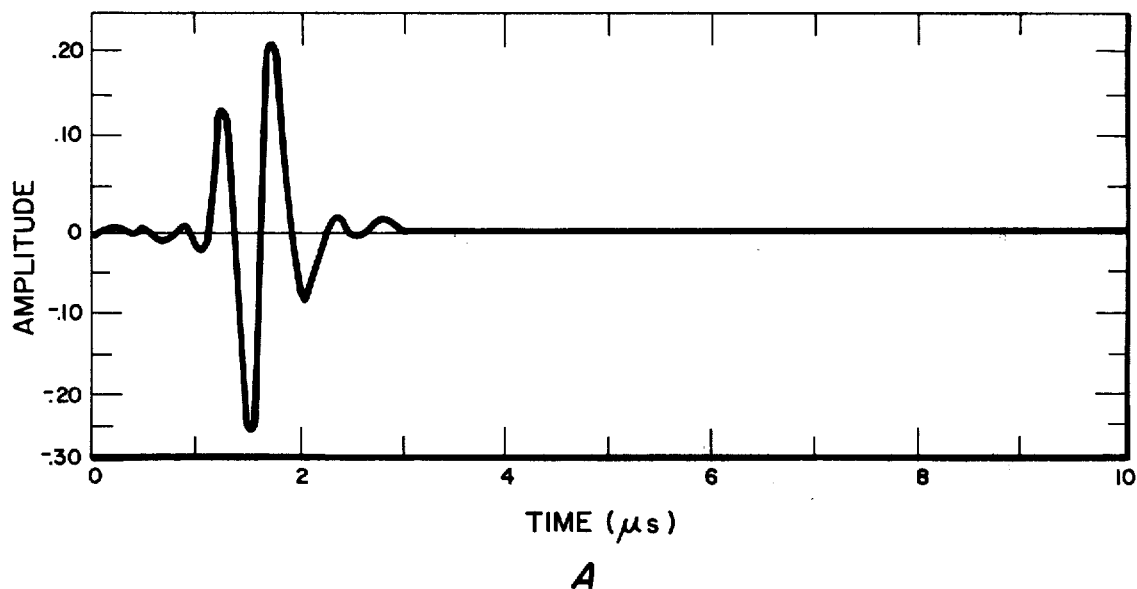
*A*
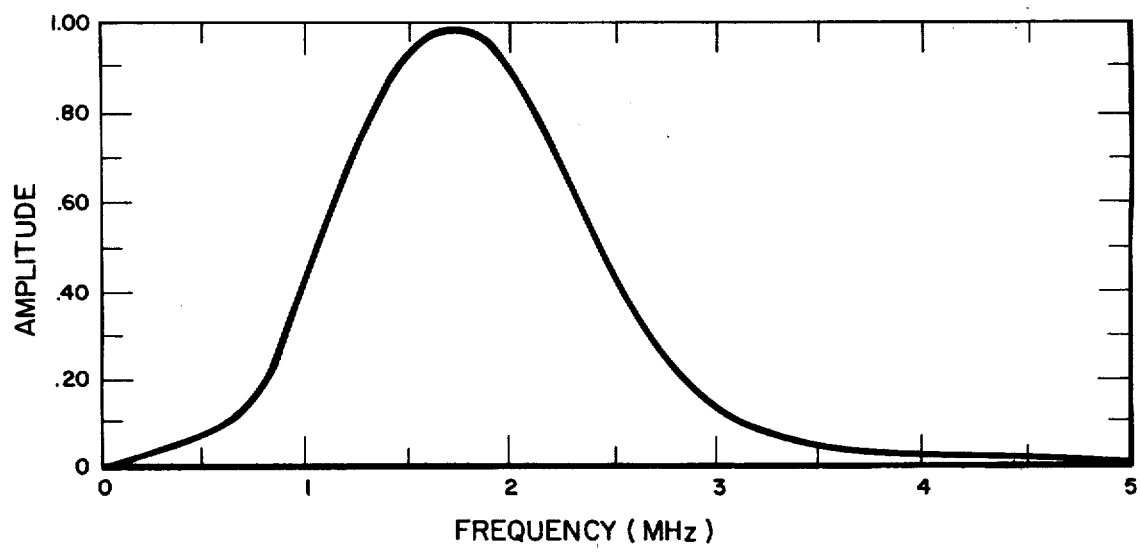
*B*
*FIG. 2.*

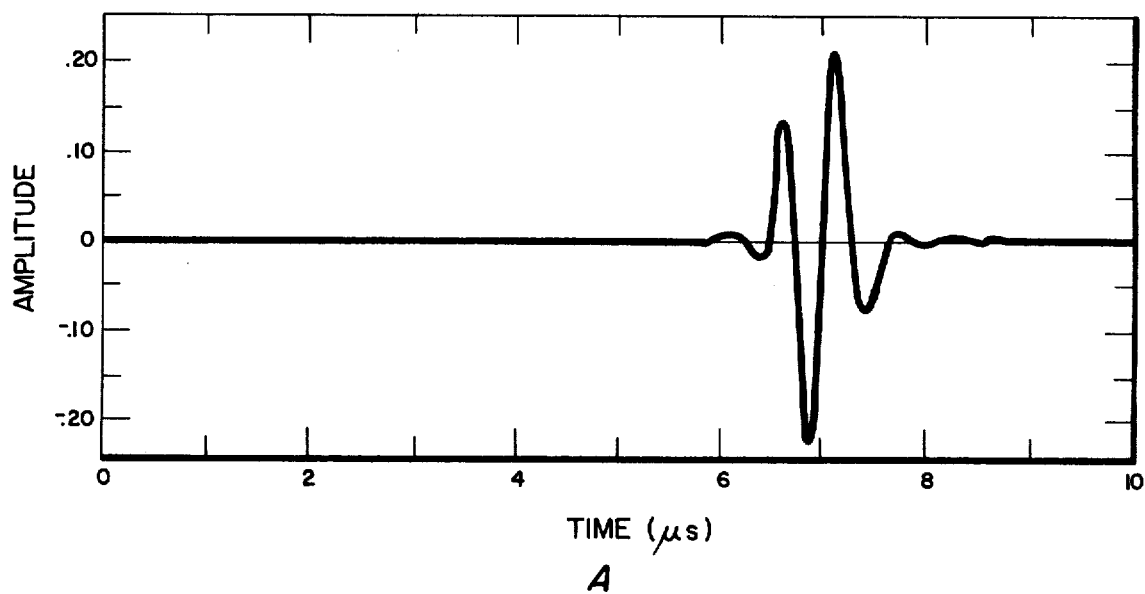
A
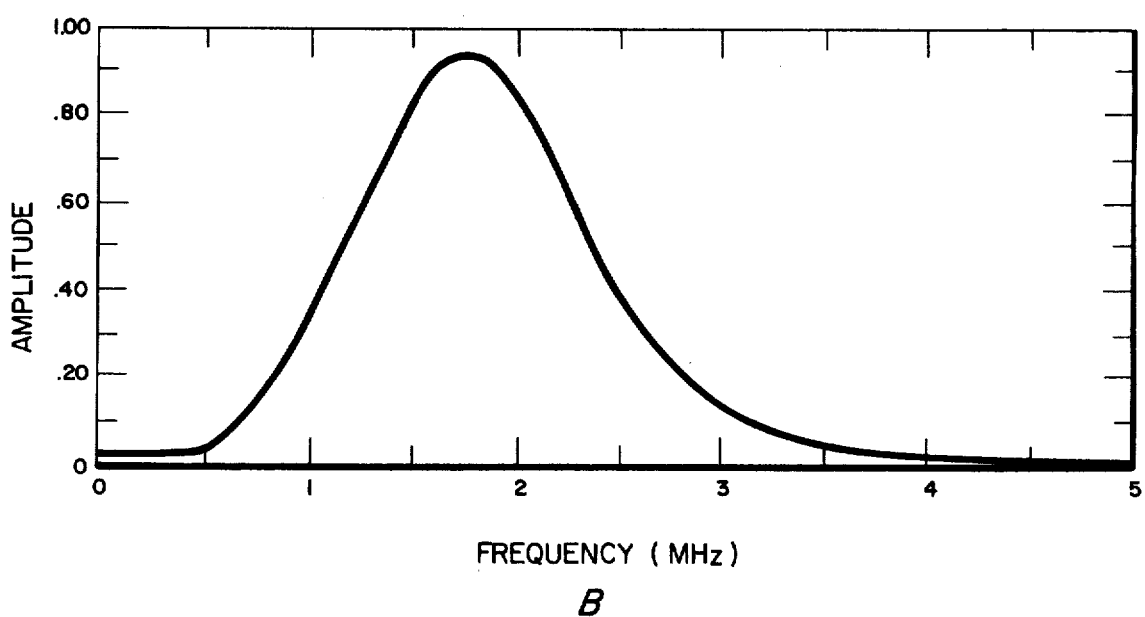
B
FIG. 3.

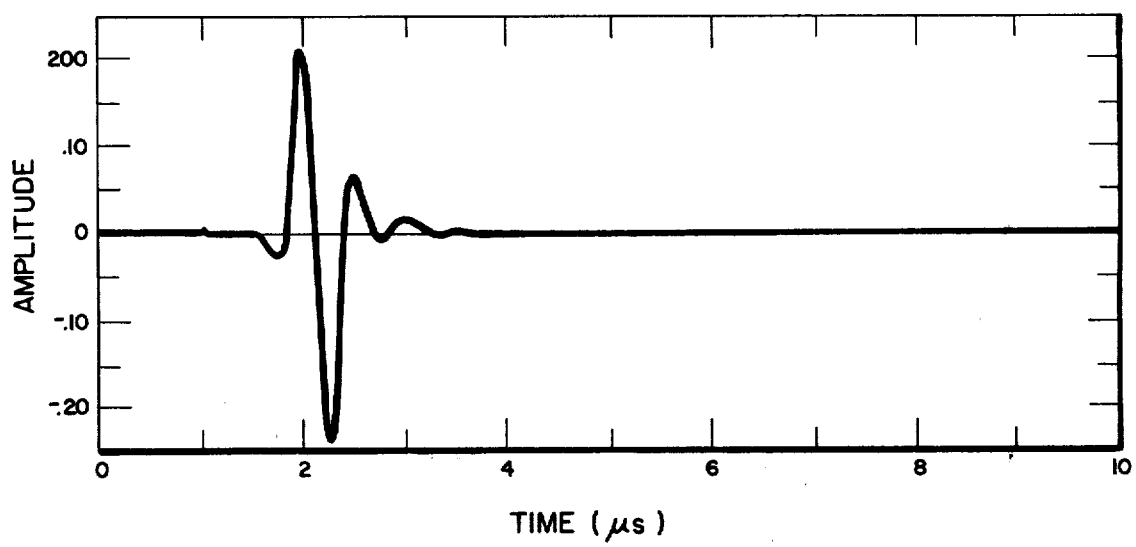
*A*
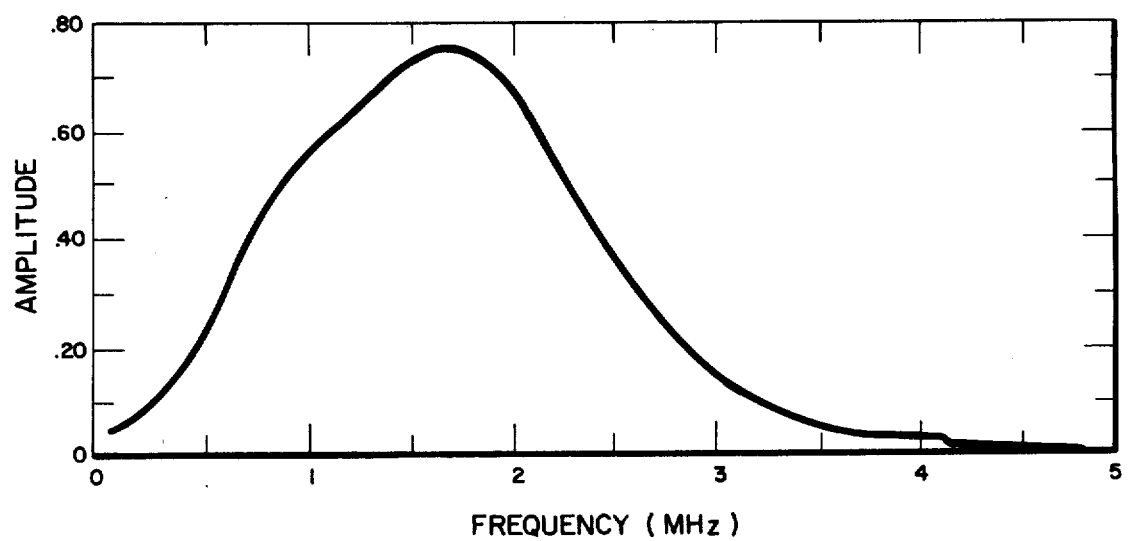
*B*
*FIG.4.*

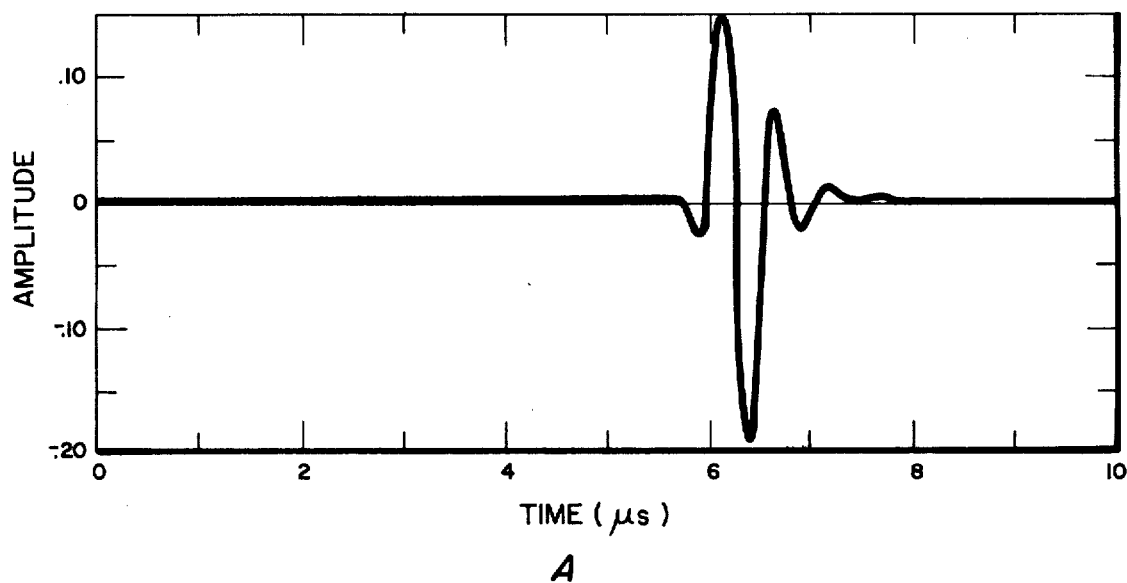
*A*
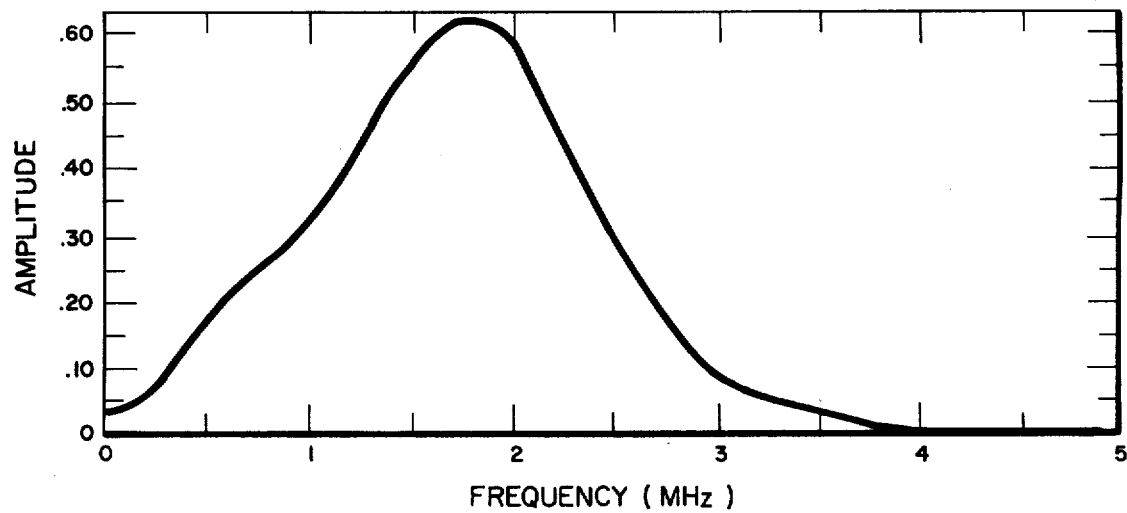
*B*
FIG.5.

ACOUSTIC MEASUREMENT OF NEAR SURFACE PROPERTY GRADIENTS

BACKGROUND OF THE INVENTION

This invention relates to nondestructive testing techniques and, more particularly, to techniques for ascertaining the surface properties of a material.

The surface properties of a material determine, to a great extent, the fatigue, wear, and corrosion characteristics of that material. Specific surface treatments, for example, may be applied to a material to inhibit deterioration and to extend the useful life of the material under adverse conditions. Because of this relationship between the surface properties and the structural characteristics of the material, the quantitative determination of surface properties has long been a goal of materials research.

Ultrasonic techniques provide one potential nondestructive approach for the measurement of surface properties. A surface acoustic wave is known to penetrate into a solid object to a depth which is roughly proportional to the wavelength of the wave. A multiple frequency wave will thus disperse (i.e., travel in the material with a frequency dependent velocity) in the presence of gradients of those physical properties which affect the velocity of the wave, such as the density and/or the elastic moduli of the object. This phenomenon of dispersive propagation makes it possible to sample the elastic properties of a material at various depths by measuring the velocity dispersion experienced by a surface acoustic wave in the material, that is, the variation of the propagation velocity as a function of the frequency of the wave. By performing an inversion of this dispersion data, the structure of the subsurface profile may then be deduced.

A known approach for obtaining such dispersion data is to inject acoustic tone bursts into the material at a limited number of discrete frequencies. This discrete frequency technique, however, yields relatively sparse dispersion data and, in addition, has been found to be too cumbersome and slow to be useful in practical applications. Consequently, a need has arisen for a new acoustic technique to quantitatively determine the surface properties of a material.

SUMMARY OF THE INVENTION

It is a general object of this invention to provide a new and improved method for determining the dispersion of a surface acoustic wave in an object.

In a first embodiment, the method includes the steps of: generating a broadband acoustic wave in a surface of the object, detecting the wave at a first location on the surface, detecting the wave at a second location on the surface, and utilizing the distance between the first and second locations and the change in phase of each frequency component of the detected wave, between the first and second locations, to calculate the dispersion of the wave in the surface.

By inverting the calculated dispersion data a subsurface profile of the physical structure of the object may be derived in order to characterize the surface properties of the object.

In another embodiment, the method includes the steps of: generating a broadband acoustic wave at first location in a surface of the object, detecting the wave at the first location after it has propagated through the surface, generating the broadband acoustic wave at a second location in the surface of the object, detecting the wave at the second location after it has propagated through the surface, and utilizing the distance between the first and second locations and the change in phase of each frequency component of the detected wave between the first and second locations to calculate the dispersion of the wave in the surface.

In a more particular embodiment, the step of calculating the dispersion of the wave further comprises calculating the velocity v(f) as a function of frequency, according to the formula $$v(f) = (2\pi f \Delta l / \Delta \phi(f))$$

or $$v(f) = (4\pi f \Delta l / \Delta \phi(f))$$

for the second embodiment, where f is the frequency component of the wave, $\Delta l$ is the distance between the first and second locations, and $\Delta \phi(f)$ is the change in phase of the frequency component f of the detected wave between the first and second locations.

The step of calculating the dispersion of the wave may further comprise taking Fourier transforms of the wave as it is detected at the first and second locations and calculating the change in phase $\Delta \phi(f)$ from the phase components of the quotient of those transforms.

The step of generating a broadband acoustic wave may further comprise energizing a transmitting acoustic transducer on the surface of the object, while the steps of detecting the wave at first and second locations may further include: positioning a receiving acoustic transducer at the first location to detect the wave, and positioning the receiving transducer at the second location to detect the wave.

In the preferred embodiment, the step of generating a broadband acoustic wave further includes generating a broadband Rayleigh wave.

These examples are provided to summarize some of the more important features of this invention, in order to introduce the more detailed description which follows and so that the contributions which this invention provides to the art may be better appreciated. There are, of course, additional features of the invention which will be further described below and which are included within the subject matter of the appended claims.

BRIEF DESCRIPTION OF THE DRAWINGS

Additional objectives, features, and advantages of the invention are discussed in the detailed description below, which refers to the following drawings:

FIG. 2A is a graphical illustration of an ultrasonic signal detected at a first location on a test object, FIG. 2B is a graphical plot of the Fourier transform which was computed for the signal shown in FIG. 2A, FIGS. 3A & B, 4A & B, and 5A & B are graphical illustrations similar to FIGS. 2A & B, but for different locations on the test object.

DETAILED DESCRIPTION OF THE INVENTION

Figure 1:
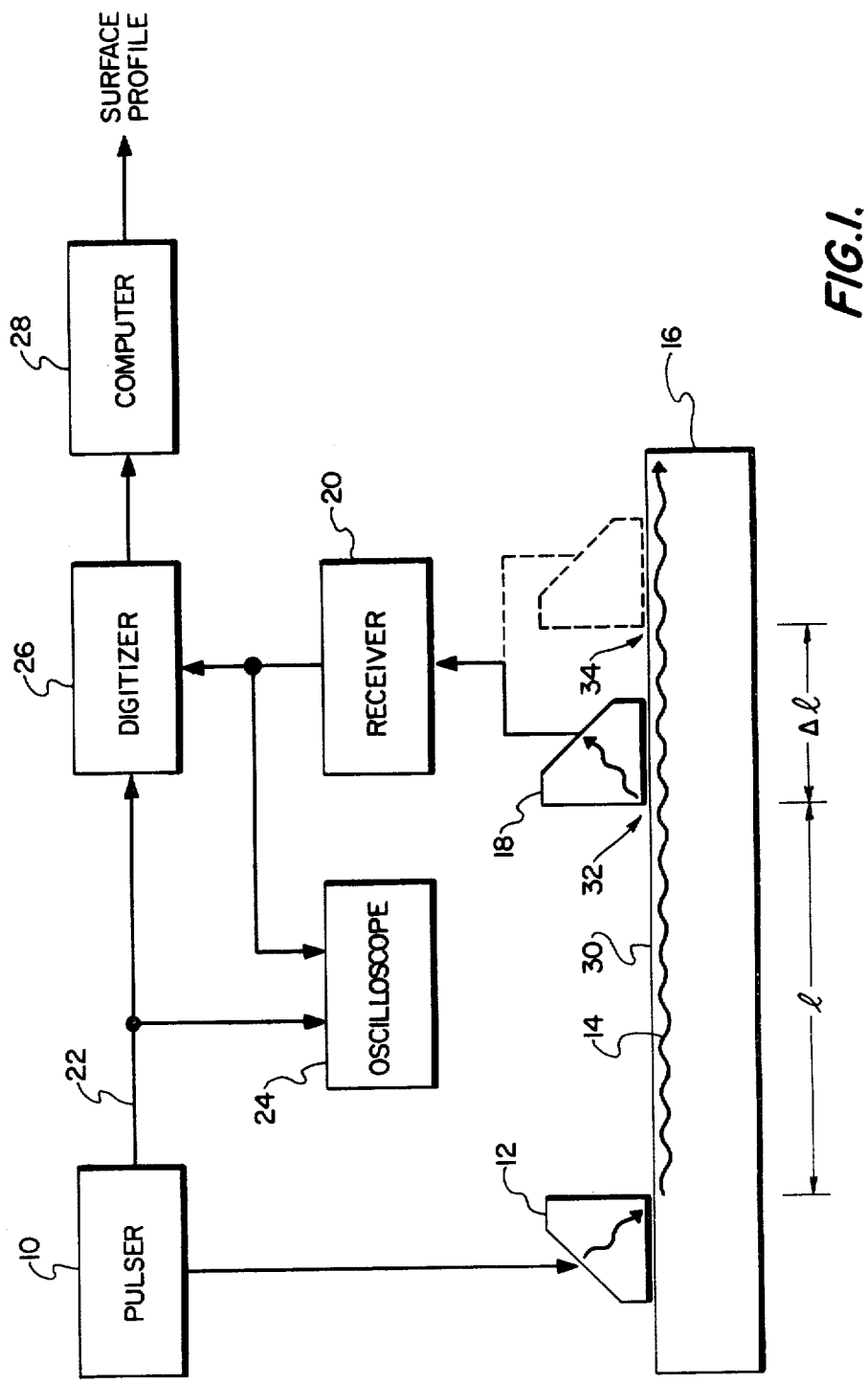
FIG. 1 is a schematic diagram of an ultrasonic testing apparatus which may be used to practice the method of the invention.

This invention is concerned with a method for measuring property gradients in a material by utilizing a dispersive acoustic surface wave generated and detected by broadband ultrasonic transducers. The technique of the invention is particularly advantageous in that it permits a dispersion curve to be determined with a minimum number of measurements providing almost complete frequency coverage. An understanding of the invention and its uses may be facilitated by a brief review of the theory which describes the relationship between the physical properties of a material and the dispersion of an acoustic wave in the material.

The Perturbation Theory Approach

The fractional changes which occur in the physical properties of a material frequently are small, making the surface wave dispersion problem amenable to treatment by a perturbation approach. This procedure may be applied to describe any variation in density or in the elastic constants as a function of depth in a material, as long as the maximum changes are sufficiently small. The perturbation model yields a linear integral relationship between velocity shifts and physical property changes, thereby providing a convenient point from which to consider the inverse problem of determining physical property gradients from measured dispersion data. A perturbation formula for the elastic surface wave case has been developed by B. A. Auld, Acoustic Waves in Fields in Solids, Chapter 12 (Wiley Interscience 1973). The basic perturbation formula, according to Auld, may be written in the form:

$$\frac{\Delta V_R}{V_R} = -\frac{V_R}{P_R} \int_0^\infty \overline{\left[ \sum_{i=1}^{3} \frac{\Delta \rho U_i^2}{2} - \sum_{I,J=1}^{6} \frac{\epsilon_I \Delta C_{IJ} \epsilon_J}{2} \right]} dz \quad (1)$$

where $V_R$ is the velocity of a Rayleigh wave in the unperturbed material, $U_i$ are the displacements and $\epsilon_I$ the strains (in reduced notation) of an unperturbed wave carrying a power $P_R$ per unit width, z is the depth coordinate inward from the surface, and $\Delta\rho$ and $\Delta C_{IJ}$ are the depth dependent changes in density and elastic stiffness.

The bar over the brackets signifies that the bracketed value is time averaged over one cycle. The physical meaning of this expression may be appreciated by noting that the first term can be associated with changes in the kinetic energy of the material, while the second term expresses the changes which occur in the stored elastic energy. In each case, the perturbation in a particular material constant is weighted by the appropriate energy density.

The perturbations in density and in the elastic constants are assumed to have the same variation with distance from the surface, i.e.,:

$$\Delta\rho = \Delta\rho^\circ F(z) \quad (2)$$

$$\Delta C_{IJ} = \Delta C^\circ_{IJ} F(z) \quad (3)$$

where the $\Delta\rho^\circ$ and $\Delta C_{IJ}^\circ$ are coefficients giving the relative strengths of the perturbations.

If, in addition, it is assumed that the unperturbed state of the solid is isotropic, then Equation 1 becomes:

$$\frac{\Delta V_R(\lambda)}{V_R} = \underline{D}^T \underline{\rho}^\circ \int_0^\infty F(z) \, \underline{E}(z/\lambda) \, d(z/\lambda) \quad (4)$$

where $\underline{\rho}^\circ$ is a 6×3 matrix containing the unperturbed material properties $\rho^\circ$ and $C^\circ_{IJ}$, $\underline{D}^T = (\Delta\rho^\circ/\rho^\circ, \Delta C^\circ_{11}/C^\circ_{11}, \Delta C^\circ_{13}/C^\circ_{13}, \Delta C^\circ_{33}/C^\circ_{33}, \Delta C^\circ_{55}/C^\circ_{55})$ and $\underline{E}^T(z/\lambda) = (e^{-2az/\lambda}, e^{-(a+b)z/\lambda}, e^{-2bz/\lambda})$ where $e^{-az/\lambda}$ and $e^{-bz/\lambda}$ are the scalar and vector potential contributions which combine to form the Rayleigh wave solution.

Equation 4 provides a starting point for considering the inversion of a set of dispersion data to obtain a surface profile of the physical properties of a material.

The Inversion Theory

To outline a technique for solving the inverse problem, it is convenient to first rewrite Equation 4 in terms of a stochastic model within the framework of statistical estimation theory. This approach provides a mathematical model which yields a probabilistic description of the possible results of a measurement. Underlying this approach are statistical ensembles of measurement errors and of all possible subsurface profiles with relative probability (a priori) weightings. The estimation procedure is equivalent to eliminating from the total ensemble those numbers which are inconsistent with the experimental data and averaging the profile in the resultant reduced ensemble.

Following this approach, Equation 4 may be rewritten as:

$$g_n = \int_0^\infty dz J_n(z) f(z) + \nu_n \quad (5)$$

where $g_n = g(k_n)$ and $J_n(z) = k_n K(k_n z)$

The quantity $k_n = 1, \ldots, n$ represents the values of the wave number for which experimental data are obtained and the quantities $\nu_n$ are the errors of these wave number measurements. g(k) is a possible value of the relative perturbation of the Rayleigh wave velocity at the wave number k, i.e., $$g(k) = \Delta V_R(k)/V_R(k) \quad (6)$$

where $V_R(k)$ is the unperturbed Rayleigh surface wave velocity and $\Delta V_R(k)$ is its perturbation at wave number k. The function f(z), a possible profile of the subsurface structure, is a single scalar measure representing the perturbations of all material properties, which are assumed to vary only with depth. Under the two assumptions of local isotropy and mutual proportionality of perturbed material properties:

$$\delta\rho(z) = \rho\omega_\rho f(z) \quad (7)$$

$$\delta\lambda(z) = \lambda\omega_\lambda f(z) \quad (8)$$

$$\delta\mu(z) = \mu\omega_\mu f(z) \quad (9)$$

where $\delta\rho(z)$, and $\delta\mu(z)$ are the perturbations of the density and two Lame constants, respectively, from their perturbed values $\rho$, g, and $\mu$.

The proportionality factors $\omega_\rho$, $\omega_\lambda$, and $\omega_\mu$ depend upon the particular assumptions made concerning the nature of the surface layer property gradients. In actual computations it may be assumed that $\omega_\rho = 0$, $\omega_\lambda = 2\mu/3\lambda$, and $\omega_\mu = 1$, corresponding to the hypothesis that the surface layer gradient leaves the density $\rho$ and the bulk modulus $\lambda + 2\mu/3$ unchanged.

The kernel function $K(x)$ has the form:

$$K(x) = \sum_{i=1}^{3} C_i e^{-\lambda_i x} \qquad (10)$$

where the parameters $c_i$ and $\lambda_i$ are related to the unperturbed material properties.

Equation 5 is the probabilistic extension of the integral Equation 4 to include measurement errors and a reinterpretation of $f(z)$ as a random process for presenting the a priori knowledge of the relative probabilities of various samples of $f(z)$. It is explicitly assumed that $f(z)$ is a gaussian random process and that the $\nu_n$ are gaussian random variables.

Using this mathematical model, the procedure for determining an estimate of the profile of subsurface properties from the measured dispersion data is to optimize a function called the estimator in a least-mean-square sense in terms of its performance in the mathematical model. The estimator is the function which gives the estimated profile in terms of the measured data. Since the model is linear and gaussian, the optimal estimator will be linear in the measured quantities and will have the form:

$$\hat{f}(z;g_n) = b(z) + \sum_{n=1}^{N} B_n(z)\Delta g_n \qquad (11)$$

The optimal estimator $\hat{f}(z;\tilde{g}_n)$ is determined by minimizing the mean-square error $$\epsilon = \tfrac{1}{2} E[\hat{f}(z;g_n) - f(z)]^2 \qquad (12)$$

where $g_n$ denotes the actual measured values, $\tilde{g}_n$ denotes the values in the random model defined by Equation (5), and E is the averaging operator.

The minimization of E yields the following for the optimal estimator:

$$\hat{f}(z;\tilde{g}_n) = Ef(z) + \sum_{n,n'}^{N} J_n(z) C_{g,nn'}^{-1}(\tilde{g}_{n'} - Eg_n) \qquad (13)$$

where $C_{g,nn'}^{-1}$ is the matrix inverse of:

$$C_{g,nn'} \triangleq E \Delta g_n \Delta g_{n'} = M_{nn'} + \sigma_n^2 \delta_{nn'}$$

The other quantities in Equation 11 are defined as:

$$M_{nn'} = \int_0^\infty dz J_n(z) J_{n'}(z) \text{ and } J_n(z) = \int_0^\infty dz' Cf(z,z') J_n(z)$$

Measuring Dispersion and Characterizing Surface Properties

The preceding mathematical models for dispersion and inversion illustrate how dispersion data can be quantitatively related to the surface properties of a material. The present invention provides a novel technique for obtaining better dispersion data to utilize this characterization technique.

FIG. 1 is a schematic diagram illustrating a preferred embodiment of an apparatus which has been used to practice the method of this invention. A pulser 10 is used to excite a transmitting transducer 12. The pulser used is a Panametrics 5052 PR, which provides a pulse 150 Volts in height and approximately 100 nano seconds wide. A number of different transducers have been used, such as piezoelectric (PZT) with a lucite wedge couplant, PZT with a water couplant, and electromagnetic acoustic. A surface wave 14 is generated in a test object 16 by the transducer 12 and is detected by a receiving transducer 18, which may be similar in design to the transducer 12. The signal developed by the transducer 18 is amplified by a receiver 20, the receiver being a Panametrics 5052 PR, with a bandwidth of 0–30 MHz and a selectable gain of 20 or 40 dB. The pulser 10 also provides a synchronizing signal 22, which is input to an oscilloscope 24 and a digitizer 26, which in the embodiment discussed here is a Tektronix 7912D Programmable Digitizer. The digitizer waveforms may be stored and manipulated by a Data General Eclipse M/600 Computer 28.

The most important part of the apparatus is the transducer system. In the preferred embodiment, a pair of matched wideband transducers was mounted on wedges at the proper angle to generate Rayleigh waves in the particular material being tested. A special jig was constructed to separate the transducers by a distance l and to precisely measure a change in distance $\Delta l$ between the transducers. In practicing the invention, the minimum distance between the generating and detecting transducers should be large enough that the receiving transducer is in the far field of the transmitting transducer. In addition, the change in distance $\Delta l$ should be known to at least 0.1% to obtain suitably accurate velocity measurements.

In order to determine the dispersion of a surface acoustic wave in the object 16 according to the "pitch-catch" embodiment of this invention, the pulser 10 and the transducer 12 are used to generate a broadband acoustic wave 14 in a surface 30 of the object. The wave is then detected at a first location 32 on the surface and at a second location 34 on the surface by the transducer 18. The receiver 20, the digitizer 26, and the computer 28 are employed, utilizing the distance between the first and second locations and the change in phase of each frequency component of the detected wave, between the first and second locations, to calculate the dispersion of the wave in the surface. The dispersion data thus obtained can be inverted to derive a subsurface profile of the physical structure of the object.

One of the important features of this invention is the determination of the velocity with which dispersive surface acoustic waves, such as Rayleigh waves, travel in the material of interest. Where the distance between the first and second locations is $\Delta l$, the effective velocity v with which a given frequency component of the broadband ultrasonic pulse will travel is $$v(f) = (\Delta l / \Delta t(f)) \qquad (14)$$

where $\Delta t(f)$ is the time required for a given frequency component to travel from one received position to the other and f is the frequency. The method of this invention will produce a display of the wave velocity as a function of frequency for all of the frequencies which are within the bandwidth of the transducers used. The velocity may be obtained by performing Fourier transforms of the two received ultrasonic waveforms. One of the received signals will arrive later in time than the other due to the change in distance $\Delta l$. This time difference is expressed in the Fourier transform as a multiplication of the transform of the later signal by a factor.

$$e^{j2\pi f\Delta t(f)} \quad (15)$$

Consequently, the phase of the two transforms differs by an amount $$\Delta\phi(f) = 2\pi f\Delta t(f) \quad (16)$$

Substituting Equation 16 into Equation 14:

$$v(f) = (2\pi f\Delta l/\Delta\phi(f)) \quad (17)$$

$\Delta\phi(f)$ may be calculated, as will be appreciated by those skilled in the art, by dividing one of the Fourier transforms by the other and determining the phase component of the quotient which is obtained.

The embodiment of the invention discussed above utilizes what is known in the art as the "pitch-catch" technique of ultrasonic testing. This invention may also be used in the "pulse-echo" mode, in which the same transducer is used to both generate and detect broadband acoustic waves. In the latter embodiment, a broadband acoustic wave is generated at a first location in the surface and detected at the first location after it has propagated through the surface. This generation and detection procedure is repeated at a second location at a distance $\Delta l$ from the first. The velocity v(f) may then be determined from the expression:

$$v(f) = (4\pi f\Delta l/\Delta\phi(f)) \quad (18)$$

Equation 18 is derived in a manner analogous to that described above with respect to Equations 14-17, but differs from equation 17 by a factor of 2, because the second wave, in the pulse-echo mode, will travel through the distance $\Delta l$ twice rather than once.

Experimental Results

Figure 6:
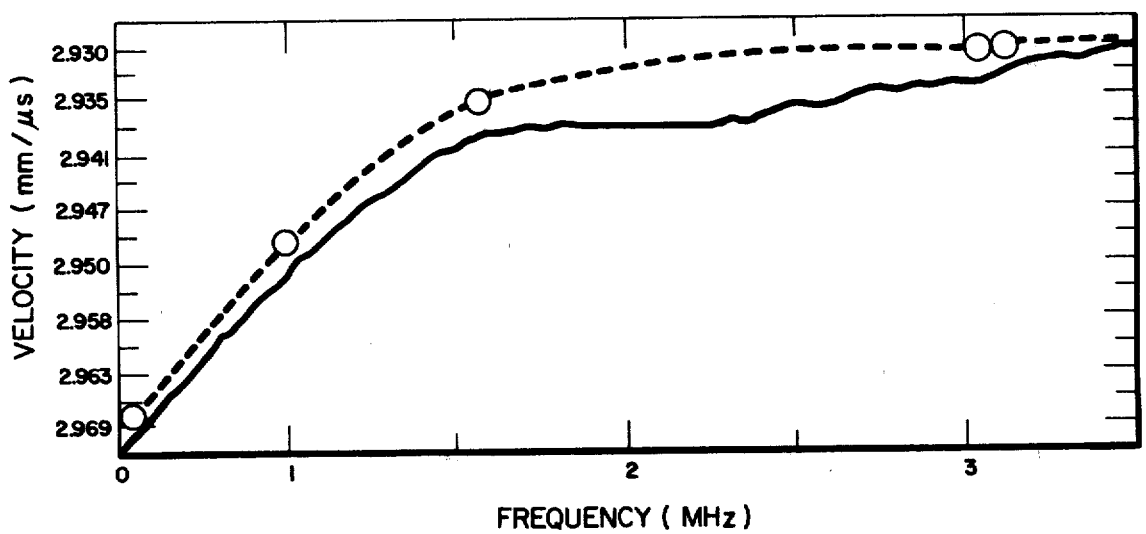
FIG. 6 is a plot of the velocity dispersion computed from the data of FIGS. 2A & B and 3A & B.
Figure 7:
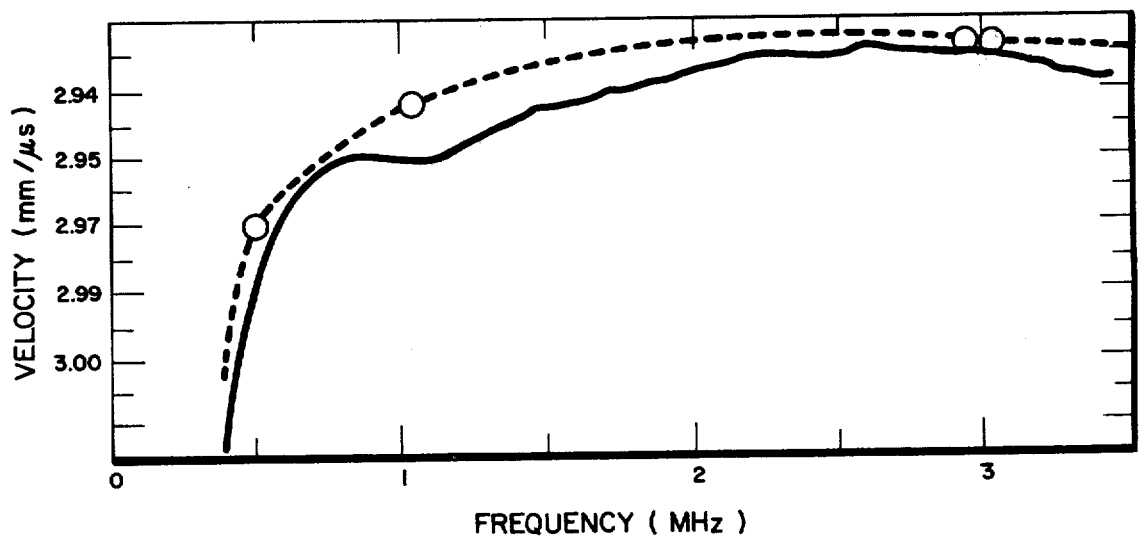
FIG. 7 is a plot of the velocity dispersion computed from the data of FIGS. 4A & B and 5A & B.

The advantages of the present invention have been verified in experiments performed on a sample of 4130 case hardened steel using 2.25 MHz transducers mounted on lucite wedges set at the Rayleigh wave critical angle for steel. These experiments were conducted in the pulse-echo mode. The results of velocity measurements for two different locations on the material are graphically illustrated in FIGS. 2-7. FIGS. 2A & B illustrate the velocity data for a measurement taken at a first location, with FIG. 2A depicting the amplitude of the detected wave as a function of time, while FIG. 2B shows the corresponding Fourier transform which was computed. Similar graphs are illustrated in FIGS. 3A & B for a second location spaced from the first. Another set of similar measurements, which were obtained from a different surface area of the test object, are shown in FIGS. 4A & B and 5A & B. The computed velocity profile for the data of FIGS. 2 and 3 is plotted as the solid line in FIG. 6 while the solid line in FIG. 7 represents the velocity profile obtained from the data of FIGS. 4 and 5. The circled points on FIGS. 6 and 7 represent dispersion data which was obtained for the test object by destructive testing methods, while the dotted lines represent the velocity profiles which should be measured according to theory. As will be appreciated by those skilled in the art, the dispersion profiles of FIGS. 6 and 7 can be inverted to determine the properties of the sampled material as a function of the depth from the surface of the material.

Although some typical embodiments of the present invention have been illustrated and discussed above, numerous modifications and additional embodiments of the invention should be apparent to those skilled in the art. Various changes, for example, may be made in the configurations, sizes, and arrangements of the components of the invention without departing from the scope of the invention. Furthermore, equivalent elements might be substituted for those illustrated and described herein, parts or connections might be reversed or otherwise interchanged, and certain features of the invention might be utilized independently of the use of other features. Consequently, the examples presented herein, which are intended to teach those skilled in the art how to perform the method of this invention, should be considered as illustrative rather than comprehensive, the appended claims being more indicative of the full scope of the invention.

What is claimed is:

1. A method for determining the dispersion of a surface acoustic wave in an object, comprising the steps of:
   generating a broadband acoustic wave in a surface of the object;
   detecting the wave at a first location on the surface;
   detecting the wave at a second location on the surface; and
   calculating the velocity dispersion $v(f) = 2\pi f\Delta l/\Delta\phi(f)$ where f is the frequency component of the wave, $\Delta l$ is the distance between the first and second locations, and $\Delta\phi(f)$ is the change in phase of the frequency component f of the detected wave between the first and second locations.

2. A method for determining the dispersion of a surface acoustic wave in an object, comprising the steps of:
   generating a broadband acoustic wave at a first location in a surface of the object;
   detecting the wave at the first location after it has propagated through the surface;
   generating the broadband acoustic wave at a second location in the surface of the object;
   detecting the wave at the second location after it has propagated through the surface; and
   calculating the velocity dispersion $v(f) = 4\pi f\Delta l/\Delta\phi(f)$ where f is the frequency component of the wave, $\Delta l$ is the distance between the first and second locations, and $\Delta\phi(f)$ is the change in phase of the frequency component f of the detected wave between the first and second locations.

3. The method of claims 1 or 2, further comprising the step of:
   inverting the calculated dispersion to derive a subsurface profile of the physical structure of the object.

4. The method of claims 1 or 2, wherein the step of calculating the dispersion of the wave further comprises taking Fourier transforms of the wave detected at the first and second locations and calculating the change in phase $\Delta\phi(f)$ from the phase components of the quotient of those transforms.

5. The method of claims 1 or 2 wherein the step of generating a broadband acoustic wave further comprises energizing a transmitting acoustic transducer on the surface of the object.

6. The method of claim 5, wherein the steps of detecting the wave at first and second locations further comprise:
   positioning a receiving acoustic transducer at the first location to detect the wave, and positioning the receiving transducer at the second location to detect the wave.

7. The method of claims 1 or 2 wherein the step of generating a broadband acoustic wave further comprises generating a broadband Rayleigh wave.

8. A method for determining the dispersion of a surface acoustic wave in an object, comprising the steps of:
generating a broadband acoustic wave in a surface of the object;
detecting the wave at a first location on the surface;
detecting the wave at a second location on the surface;
calculating a Fourier transform of the first detected wave;
calculating a Fourier transform of the second detected wave;
calculating the change in phase $\Delta\phi(f)$ of the frequency component f of the detected wave between the first and second locations from the phase component of the quotient of the transforms; and
calculating the dispersion of the wave in the surface according to the formula $$v(f) = (2\pi f \Delta l / \Delta\phi(f))$$

where $v(f)$ is the velocity of the wave in the surface as a function of frequency and $\Delta l$ is the distance between the first and second locations.

9. A method for determining the dispersion of a surface acoustic wave in an object, comprising the steps of:
generating a broadband acoustic wave at a first location in a surface of the object;
detecting the wave at the first location after it has propagated through the surface;
generating the broadband acoustic wave at a second location in the surface of the object;
detecting the wave at the second location after it has propagated through the surface;
calculating a Fourier transform of the first detected wave;
calculating a Fourier transform of the second detected wave;
calculating the change in phase $\Delta\phi(f)$ of the frequency component f of the detected wave between the first and second locations from the phase component of the quotient of the transforms; and
calculating the dispersion of the wave in the surface according to the formula $$v(f) = (4\pi f \Delta l / \Delta\phi(f))$$

where $v(f)$ is the velocity of the wave in the surface as a function of frequency and $\Delta l$ is the distance between the first and second locations.

* * * * *